United States Patent [19]

Fukamachi et al.

[11] Patent Number: 4,929,774

[45] Date of Patent: May 29, 1990

[54] STABLE MIXTURE CONTAINING OXIDATION-SENSITIVE COMPOUNDS, PREPARATION THEREOF AND USE OF A COMBINATION OF SUBSTANCES FOR STABILIZING OXIDATION-SENSITIVE COMPOUNDS

[75] Inventors: Chiharu Fukamachi, Uedashi, Japan; Horst Schumacher, Bobenheim am Berg, Fed. Rep. of Germany; Wolfgang Bewert, Frankenthal, Fed. Rep. of Germany; Joachim Schneider, Weisenheim am Berg, Fed. Rep. of Germany

[73] Assignee: BASF Aktiengesellschaft, Ludwigshafen, Fed. Rep. of Germany

[21] Appl. No.: 302,611

[22] Filed: Jan. 27, 1989

[30] Foreign Application Priority Data

Jan. 1, 1988 [JP] Japan ................. 63-17232

[51] Int. Cl.$^5$ ............................................. C07C 35/18
[52] U.S. Cl. ..................................... 568/824; 568/825
[58] Field of Search ........................ 568/824, 702, 825

Primary Examiner—Werren B. Lone
Attorney, Agent, or Firm—Oblon, Spivak, McClelland, Maier & Neustadt

[57] ABSTRACT

A stable mixture of an oxidation-sensitive compound contains triglycerides, complexing agents and coating substances as well as the oxidation-sensitive compound.

16 Claims, No Drawings

STABLE MIXTURE CONTAINING OXIDATION-SENSITIVE COMPOUNDS, PREPARATION THEREOF AND USE OF A COMBINATION OF SUBSTANCES FOR STABILIZING OXIDATION-SENSITIVE COMPOUNDS

The present invention relates to a stable mixture containing oxidation-sensitive compounds, to a process for preparing said mixture, and to the use of a combination of substances for stabilizing oxidation-sensitive compounds.

When oxidation-sensitive compounds, in particular fat-soluble vitamins, come into contact with air, an undesirable oxidation takes place. This reduces the quality of the products containing these sensitive compounds. Particularly when oxidation-sensitive compounds are used in foods, foodstuffs or drugs, the oxidation-sensitive compounds are destroyed by oxidation in the course of storage and the proportion of these compounds remaining in the product decreases.

To prevent this oxidation, it is possible for example to treat vitamins, oils and fats with a combination of antioxidants and sequestrants; cf. E. Furia, Handbook of Food Additives, 2nd edition, pages 271 and 274 to 281 (1975), where it is reported that the combined action of sequestrants and antioxidants is synergistic. The sequestrants proposed comprise a large number of different compounds, for example salts of acetic acid, salts of citric acid, ethylenediaminetetraacetate, calcium phytate, sodium thiosulfate and the like. This reference also mentions triglycerides, though not as stabilizing agents but, on the contrary, as substrates to be stabilized; cf. ibid page 280.

JP-A-9204-696 proposes a combination of phytic acid, dl-α-tocopherol, natural vitamin E or vitamin C for use as an antioxidant for oils, fatty acids and foods containing these constituents.

Various methods have been proposed for stabilizing vitamin A. For instance, vitamin A can be converted into the acetic ester or a fatty ester, for example a palmitic ester, and a synthetic oxidation inhibitor can be added. Suitable oxidation inhibitors here are dibutylhydroxytoluene (BHT), butylhydroxyanisole (BHA), nordihydroguajaretic acid (NDGA), propyl galate (PG) or N,N'-diphenylparaphenylenediamine (DPPD). Another way of stabilizing vitamin A is to coat vitamin A with gelatin, casein, dextrin or other substances in order to cut off the access of air, and then to prepare beadlets or powders. Another possibility is to convert vitamin A in the presence of natural phenolic substances and ascorbic acid into granular or pulverulent solids; cf. JP-A-122,424/84.

However, the prior art proposals for stabilizing oxidation-sensitive compounds are not adequate, since neither adequate coating of the sensitive compounds nor adequate protection from oxidation-promoting heavy metal traces is obtained.

It is an object of the present invention to provide a stable mixture of oxidation-sensitive compounds which is stable and easy to handle and is suitable in particular for foods, feedstuffs and pharmaceutical applications.

We have found that this object is achieved by providing a stable mixture containing an oxidation-sensitive compound, a triglyceride, a complexing agent and a coating substance.

The combination of a triglyceride, a complexing agent and a coating substance surprisingly confers full protection on the oxidation-sensitive compound. While the individual components of the combination of these three active substances have only a small protective effect, the combination gives a superadditive protective effect.

In a preferred embodiment of the invention, the mixture additionally contains customary antioxidants. They can comprise, for example, BHT, BHA and ethoxyquin.

In a further preferred embodiment, the triglyceride is a vegetable oil. The triglycerides usable in the invention include natural products, triglycerides regenerated from natural products, and synthetic triglycerides. It is possible to use one or more of these triglycerides. Preference is given to using vegetable oils such as olive oil, soybean oil, corn oil, cotton seed oil, sunflower oil, peanut oil, palm oil, coconut oil and wheatgerm oil, but it is also possible to use various animal fats (for example pig fat, cattle fat, sheep fat and fish oils) and semisynthetic fats which are obtained by transesterification and recombination, including fractionation and hydrogenation.

In a further preferred embodiment, the complexing agent is phytic acid, phosphoric acid, meta-, pyro or polyphosphoric acid or a salt thereof. Suitable salts are in particular metal salts (sodium, potassium, calcium).

The complexing agents also include sequestrants for the heavy metal ions and chelating agents. In particular in the case of foods it is possible to use those mentioned in the literature [for example Thomas E. Furia, Handbook of Food Additives, 2nd edition, CRC Press, pp. 271-281 (1975)]. For instance, it is also possible to use carboxylic acids, polycarboxylic acids, hydroxycarboxylic acids, amino acids, tartaric acid, gluconic acid, citric acid and ethylenediaminetetraacetic acid and metal salts thereof (for example calcium phytate, sodium pyrophosphate, sodium hexametaphosphate, sodium tripolyphosphate, sodium tartrate, calcium gluconate, sodium citrate and sodium ethylenediaminetetraacetate), citric esters, sodium nitrilotriacetate (NTA-Na), cystein, fumaric acid, maleic acid and lactic acid.

It is also possible to use combinations of complexing agents.

In a further preferred embodiment of the invention, the coating substance is a film former, in particular a protein such as gelatin or casein, or a sugar or polysaccharide, in particular gum arabic, an alginate or a starch derivative. A suitable sugar is in particular sucrose, glucose or lactose. It is also possible to antioxidants, for example BHT, BHA or ethoxyquin, flow control agents, for example silicon dioxide, calcium stearate or calcium phosphate, and also fillers, such as starch, kaolin and silicates.

The ratio of triglycerides and complexing agents to the oxidation-sensitive compounds which are to be included in the mixtures according to the invention can vary with the actual compounds used in a specific example. Based on 1 part by weight of oxidation-sensitive compound it is possible for example to use triglycerides within the range from 1 to 0.01 part by weight and complexing agents within the range from 1 to 0.01 part by weight.

The oxidation-sensitive compounds thus mixed with triglycerides and complexing agents are coated with coating substances in an amount required to obtain full coating of this mixture.

The subject matter of the invention is also a process for preparing the mixture according to the invention, which comprises preparing a dispersion from an oxidation-sensitive compound, a triglyceride, a complexing agent and a coating substance and converting this dispersion into a solid substance.

In general, the mixture according to the invention is obtained by preparing an aqueous dispersion by dispersing an oxidation-sensitive compound in triglycerides, complexing agents, coating substances and in assistants if used, converting this dispersion in a conventional manner into a solid substance and if necessary following up with a drying process. Such a process gives a stable mixture of oxidation-sensitive compounds, comprising the oxidation-sensitive compounds, coating substances, triglycerides and complexing agents.

In the process according to the invention, an aqueous dispersion or emulsion is normally prepared by first dissolving the water-soluble substances, such as coating substances, which are hydrophilic components, and other assistants in water to obtain an aqueous solution and at the same time premixing the fat-soluble substances, such as the oxidation-sensitive compounds and triglycerides. By mixing the solution with the premix using a suitable stirrer or homogenizer everything becomes dispersed or emulsified. The dispersion obtained is converted by freeze drying, vacuum drying, spray drying or convection drying into a granular or pulverulent solid substance or the solid substance is granulated in a suitable process and the granules are then dried once more.

In the process according to the invention, the drying process may be followed by an additional treatment to crosslink the coating. If gelatin is used as coating substance, for example, it is possible to crosslink with aldehydes or to carry out a thermal crosslinking treatment. It is also possible to follow the drying process by applying a further coating, for example of fats, paraffin, waxes, synthetic polymers, such as cellulose acetate, phthalate and the like.

Particularly preferably, the solid substance is present in a granular or pulverulent form, in which case an average particle size of from 100 to 600 μm is particularly favorable.

The oxidation-sensitive compounds mentioned in the present invention include fat-soluble vitamins, carotenoids, vitamin A acid and compounds derived therefrom, analogous retinoids, flavorings (for example lemon oil), scents and the like. It is possible to use one or more of these compounds. Fat-soluble vitamins include for example vitamin A, vitamin E, vitamin D, the vitamins of the K series and mixtures of these vitamins, which can be present not only in their free form but also in the form of esters. Carotenoids include for example β-carotene, canthaxanthene, citranaxanthene, ethyl β-apo-8'-carotenate, astaxanthene, xanthophylls, such as lutein and zeaxanthene, and also mixtures of these carotenoids.

However, the mixtures according to the invention may also contain other non-oxidation-sensitive constituents.

In what follows, the invention is explained in more detail by reference to non-limiting working and application examples.

WORKING EXAMPLE 1

220 parts of gelatin, 36 parts of sugar and 96 parts of dextrin were introduced into 600 parts of water and dissolved therein by heating to 70° C. Elsewhere, 220 parts of vitamin A acetate to which 3.8 parts of vitamin $D_3$ and 7.2 parts of BHT had been added were made homogeneous by melting. The mixture thus obtained was admixed with 44 parts of soybean oil and 72 parts of ethoxyquin by stirring to give a homogeneous mixture. Thereafter 20 parts of 50% strength phytic acid were added to the abovementioned aqueous solution, followed by the aforementioned vitamin solution to obtain, by dispersing and mixing, a vitamin dispersion. This dispersion was passed into a spray tower and sprayed. It was then dried in a fluidized bed dryer to obtain a stable vitamin $A/D_3$ powder.

WORKING EXAMPLE 2

53 parts of gelatin and 113 parts of glucose sirup were added to 100 parts of water and, after 30 minutes for swelling the gelatin, dissolved by heating to 70° C. Thereafter different amounts of a triglyceride and a complexing agent were added in succession, followed by 50.1 parts of vitamin A acetate which had been stabilized by the addition of 4.5 mg of BHT million I.U. and 100 mg of ethoxyquin/million I.U. A further 70 parts of water were added, and the mixture was emulsified by vigorous stirring. The emulsion obtained was finally sprayed at 70° C. by means of a commercially available spray gun into a nitrogen atmosphere laden with hydrophobic silica. The product obtained was subsequently dried at room temperature in a fluidized bed dryer in a stream of nitrogen.

Working example 2 was repeated using the following amounts of triglyceride and complexing agent in the formulation (the stated parts by weight are each based on 100 parts by weight of dry powder; where a formulation calls for an addition of additives, correspondingly less glucose sirup was used):

WORKING EXAMPLE 2-1

No complexing agent or triglyceride added.

WORKING EXAMPLE 2-2

5% addition of soybean oil, no complexing agent added.

WORKING EXAMPLE 2-3

5% addition of peanut oil, no complexing agent added.

WORKING EXAMPLE 2-4

5% addition of corn oil, no complexing agent added.

WORKING EXAMPLE 2-5

1% addition of phytic acid, no complexing agent added.

WORKING EXAMPLE 2-6

1% addition of phytic acid, 5% addition of soybean oil.

WORKING EXAMPLE 2-7

1% addition of phytic acid, 5% addition of soybean oil.

WORKING EXAMPLE 2-8

1% addition of phytic acid, 2% addition of soybean oil.

WORKING EXAMPLE 2-9

1% addition of phytic acid, 10% addition of soybean oil.

WORKING EXAMPLE 2-10

1% addition of phytic acid, 5% addition of peanut oil.

WORKING EXAMPLE 2-11

1% addition of phytic acid, 5% addition of corn oil.

WORKING EXAMPLE 2-12

1% addition of sodium salt of phytic acid, 5% addition of soybean oil.

WORKING EXAMPLE 2-13

1% addition of calcium salt of phytic acid, 5% addition of soybean oil.

WORKING EXAMPLE 2-14

1% addition of citric acid, 5% addition of soybean oil.

WORKING EXAMPLE 2-15

1% addition of sodium citrate, 5% addition of soybean oil.

WORKING EXAMPLE 2-16

1% addition of tartaric acid, 5% addition of soybean oil.

WORKING EXAMPLE 2-17

1% addition of sodium tartrate, 5% addition of soybean oil.

WORKING EXAMPLE 2-18

1% addition of salicylic acid, 5% addition of soybean oil.

WORKING EXAMPLE 2-19

1% addition of gluconic acid, 5% addition of soybean oil.

WORKING EXAMPLE 2-20

1% addition of phosphoric acid, 5% addition of soybean oil.

WORKING EXAMPLE 2-21

1% addition of sodium pyrophosphate, 5% addition of soybean oil.

WORKING EXAMPLE 2-22

1% addition of sodium hexametaphosphate, 5% addition of soybean oil.

WORKING EXAMPLE 2-23

1% addition of sodium tripolyphosphate, 5% addition of soybean oil.

WORKING EXAMPLE 2-24

1% addition of EDTA-Na(Titriplex ® III), 5% addition of soybean oil.

WORKING EXAMPLE 2-25

1% addition of NTA-Na(Titriplex I), 5% addition of soybean oil.

WORKING EXAMPLE 2-26

1% addition of cysteine, 5% addition of soybean oil.

WORKING EXAMPLE 2-27

0.5% addition of phytic acid, 5% addition of soybean oil.

WORKING EXAMPLE 2-28

1% addition of sodium phytate, 5% addition of Myglyol ® 812 (synthetic fatty acid triglyceride).

WORKING EXAMPLE 2-29

1% addition of sodium citrate, no triglyceride added.

WORKING EXAMPLE 2-30

1% addition of phosphoric acid, no triglyceride added.

WORKING EXAMPLE 2-31

1% addition of sodium hexametaphosphate, 5% addition of peanut oil.

WORKING EXAMPLE 2-32

1% addition of sodium hexametaphosphate, no triglyceride added.

WORKING EXAMPLE 2-33

1% addition of Triplex III, no triglyceride added.

WORKING EXAMPLE 2-34

1% addition of cysteine, no triglyceride added.

WORKING EXAMPLE 3

52.3 parts by weight of gelatin were made to swell in 150 parts of water after the addition of 126.8 parts of glucose sirup at room temperature, and thereafter the mixture was heated to 65° C. After addition of 50 parts of tocopherol, the mixture was emulsified at that temperature by vigorous stirring for 20 minutes. The emulsion was then sprayed by a one-material nozzle into a nitrogen atmosphere laden with hydrophobic silica. The product particles formed were dried in a nitrogen stream on a glass suction filter until the residual moisture content was 3%.

Working example 3 was repeated using the following amounts of a fatty acid triglyceride and a complexing agent in the formulation, the stated parts by weight each being based on 100 parts by weight of the dry powder obtained:

WORKING EXAMPLE 3-1

No complexing agent or fatty acid triglyceride or vegetable oil added.

WORKING EXAMPLE 3-2

No complexing agent added, 5% addition of soybean oil.

WORKING EXAMPLE 3-3

1% addition of sodium hexametaphosphate, no vegetable oil added.

WORKING EXAMPLE 3-4

1% addition of sodium hexametaphosphate, 5% addition of soybean oil.

WORKING EXAMPLE 4

In accordance with the directions of working example 3, 52.3 parts of gelatin were swollen in 122 parts of glucose sirup in 180 parts of water and heated to 60° C., 52.4 parts of vitamin A acetate (2.1 million I.U./g), stabilized with 100 mg of ethoxyquin/million I.U. and 0.55 parts of vitamin $D_3$ (40 million I.U./g), were added, and the mixture was emulsified for 20 minutes. The emulsion obtained was sprayed as described, and the product obtained was then dried in a stream of nitrogen.

Working example 4 was repeated using in addition to the stated substances the following amounts of a fatty acid triglyceride and of a complexing agent in the formulation, the stated parts by weight each being based on 100 parts of the dry powder obtained:

WORKING EXAMPLE 4-1

No complexing agent or vegetable oil added.

WORKING EXAMPLE 4-2

1% addition of phytic acid and 5% addition of soybean oil.

WORKING EXAMPLE 5

WORKING EXAMPLE 5-1

A citranaxanthene dispersion consisting of
4.9% of citranaxanthene (micronized)
0.3% of ascorbyl palmitate
1.6% of ethoxyquin
14.6% of gelatin 100 bloom
13.1% of sucrose
65.5% of water
was sprayed at 50° C. with a one-material nozzle under 6.0 to 6.5 bar in a spray tower into a cloud of hydrophobic silica. The moist product was dried on a fluidized bed dryer at room temperature to a residual moisture content of about 4%. The active substance content of the powder was 13.7%.

WORKING EXAMPLE 5-2

A citranaxanthene dispersion consisting of
4.3% of citranaxanthene (micronized)
0.3% of ascorbyl palmitate
1.4% of ethoxyquin
12.7% of gelatin 100 bloom
9.7% of sucrose
1.6% of soybean oil
70% of water
was treated as in 5-1. The active substance content of the powder was 13.2%.

WORKING EXAMPLE 5-3

A citranaxanthene dispersion consisting of
4.5% of citranaxanthene (micronized)
0.3% of ascorbyl palmitate
1.5% of ethoxyquin
13.2% of gelatin 100 bloom
9.7% of sucrose
1.7% of soybean oil
0.4% of phytic acid (as Na salt)
68.7% of water
was treated as in 5-1. The active substance content of the powder was 13.2%.

WORKING EXAMPLE 5-4

A citranaxanthene dispersion consisting of
4.8% of citranaxanthene (micronized)
0.3% of ascorbyl palmitate
1.5% of ethoxyquin
13.5% of gelatin 100 bloom
9.7% of sucrose
1.8% of soybean oil
0.4% of ethylenediaminetetraacetic acid (as Na salt)
was treated as in 5-1. The active substance content of the powder was 13.0%.

WORKING EXAMPLE 6

WORKING EXAMPLE 6-1

200 parts of a dispersion consisting of 106.8 parts of water, 1.1 part of a preservative mix, 3.8 parts of ethoxyquin, 47.3 parts of sucrose, 29 parts of gelatin (type B 200) and 13.3 parts of micronized canthaxanthene were dispersed at 40° C. in 400 parts of paraffin oil, by vigorous stirring. After cooling down to 18° C., the surface of the particles formed was powdered by addition of corn starch. The product, which was now present in the form of small balls from 50 to 500µ in diameter, was washed in 2000 parts of cold petroleum ether and finally dried on a fluidized bed dryer at room temperature to a residual moisture content of 4%. The active substance content of the powder was 10.7%.

WORKING EXAMPLE 6-2

Working example 6-1 was repeated, except that an additional 4.0 parts of soybean oil and 0.8 part of phytic acid was added to the emulsion, affording, after work-up in a similar manner to working example 6-1, a powder having a canthaxanthene content of 10.1%, a phytic acid content of 1% and a soybean oil content of 5%.

APPLICATION EXAMPLE 1

Testing of vitamin A/$D_3$-containing dry powders 1.0 g of the powder of working example 1 was introduced into a glass bottle without premix, and this glass bottle was stored at a constant temperature of 40° C. and 70% relative humidity, and the remaining proportion of vitamin A was measured at intervals. The result is shown in the table below.

10 g of the powder of working example 1 were mixed with 40 g of premix substrate comprising 50% of wheat middlings, 30% of 50% strength choline chloride and 10% of a trace element mixture. 3.2% of the premix thus obtained were introduced into a glass bottle which was then covered with aluminium foil instead of a lid and 5 holes were made in the aluminum foil for ventilation. This bottle was placed in a container at a constant temperature of 40° C. and a constant relative humidity of 70% and the remaining proportions (retention %) of vitamin A was measured at certain times. The above-mentioned trace elements comprised a mixture of 37.44% of $CuSO_4 \times 5\ H_2O$, 46.78% of $FeSO_4 \times 7\ H_2O$, 11.78% of ZnO; 3.61% of MnO and 0.39% of $CoCO_3$.

The test results are shown in the following table I:

TABLE I

| | Vitamin A retention (%) | | |
|---|---|---|---|
| Test | Days | after 1 month (%) | aftr 2 months (%) |
| Powder of working example 1 | 100 | 90 | 86 |
| Premix mixed with the powder of working | 100 | 63 | 52 |

TABLE I-continued

| Test | Days | Vitamin A retention (%) after 1 month (%) | aftr 2 months (%) |
|---|---|---|---|
| example 1 Powder similar to working example 1 but without soybean oil and phytic acid | 100 | 59 | 40 |

APPLICATION EXAMPLE 2

Testing of vitamin A-containing dry powders

1% by weight of the individual powders of working example 2 were mixed with 99% of the premix mentioned in application example 1. 4 g samples of these mixtures were tested at the beginning and after 4 weeks storage in a conditioning cabinet at 40° C. and 70% relative humidity in respect of their vitamin A content. The proportion remaining after 4 weeks is reported as a % age of the starting value of the storage in the following tables II and III:

TABLE II

Vitamins A (relating to application example 2)

| Working example No. | Complexing agent | Oil | Retention (%) after 4 weeks |
|---|---|---|---|
| 2-1 | — | — | 17 |
| 2-2 | — | 5% of soybean oil | 32 |
| 2-3 | — | 5% of peanut oil | 31 |
| 2-4 | — | 5% of corn oil | 46 |
| 2-5 | 1% of phytic acid | — | 24 |
| 2-6 | 1% of phytic acid | 5% of soybean oil | 47 |
| 2-7 | 1.5% of phytic acid | 5% of soybean oil | 53 |
| 2-8 | 1% of phytic acid | 2% of soybean oil | 55 |
| 2-9 | 1% of phytic acid | 10% of soybean oil | 59 |
| 2-10 | 1% of phytic acid | 5% of peanut oil | 53 |
| 2-11 | 1% of phytic acid | 5% of corn oil | 54 |
| 2-12 | 1% of sodium phytate | 5% of soybean oil | 58 |
| 2-13 | 1% of calcium phytate | 5% of soybean oil | 59 |
| 2-14 | 1% of citric acid | 5% of soybean oil | 46 |
| 2-15 | 1% of sodium citrate | 5% of soybean oil | 53 |
| 2-16 | 1% of tartaric acid | 5% of soybean oil | 49 |
| 2-17 | 1% of sodium tartrate | 5% of soybean oil | 55 |
| 2-18 | 1% of salicyclic acid | 5% of soybean oil | 53 |
| 2-19 | 1% of gluconic acid | 5% of soybean oil | 50 |
| 2-20 | 1% phosphoric acid | 5% of soybean oil | 63 |
| 2-21 | 1% of sodium pyrophosphate | 5% of soybean oil | 57 |
| 2-22 | 1% of sodium hexametaphosphate | 5% of soybean oil | 53 |
| 2-23 | 1% of sodium tripolyphosphate | 5% of soybean oil | 57 |
| 2-24 | 1% of EDTA sodium (Titriplex III) | 5% of soybean oil | 59 |
| 2-25 | 1% of NTA sodium (Titriplex I) | 5% of soybean oil | 51 |
| 2-26 | 1% of cysteine | 5% of soybean oil | 59 |
| 2-27 | 0.5% of phytic acid | 5% of soybean oil | 29 |

TABLE III

Vitamin A (relating to application example 2)

| Working example No. | Complexing agent | Oil | Retention (%) after 4 weeks |
|---|---|---|---|
| 2-28 | 1% of sodium phytate | 5% of synthetic triglyceride* | 54 |
| 2-29 | 1% of sodium citrate | — | 13 |
| 2-30 | 1% of phosphoric acid | — | 55 |
| 2-31 | 1% of sodium hexametaphosphate | 5% of peanut oil | 44 |
| 2-32 | 1% of sodium hexametaphosphate | — | 28 |
| 2-33 | 1% of EDTA sodium (Titriplex III) | — | 20 |
| 2-34 | 1% of cystein | — | 25 |

*Myglyol 812 (neutral oil) = caprylic caproic triglyceride

APPLICATION EXAMPLE 3

Testing of tocopherol-containing dry powders

1% by weight of the individual powders of working example 3 were mixed with 99% of the premix mentioned in application example 1. 6 g samples of these mixtures were tested at the start and after 4 weeks' storage in a conditioning cabinet at 40° C. and 70% relative humidity in respect of their tocopherol content. The proportion remaining after 4 weeks is reported as a percentage of the starting value of the storage in the following table:

| Working example No. | Complexing agent | Oil | Retention (%) after 4 weeks |
|---|---|---|---|
| 3-1 | — | — | 18 |
| 3-2 | — | 5% of soybean oil | 23 |
| 3-3 | 1% of sodium hexametaphosphate | — | 41 |
| 3-4 | 1% of sodium hexametaphosphate | 5% of soybean oil | 49 |

APPLICATION EXAMPLE 4

Testing of vitamin $D_3$-containing dry powders

Vitamin A/$D_3$ dry powder of working example 4 was tested in the same premix as in application example 5. 2 million I.U. of vitamin $D_3$ were mixed in per kg of premix. 10 g samples of the ready-prepared mixtures were tested at the start and after 4 and 8 weeks storage in a conditioning cabinet at 40° and 70% relative humidity in respect of their vitamin $D_3$ content. The proportion remaining after 8 weeks is reported as a percentage of the starting value of the storage in the following table:

| Working example No. | Complexing agent | Oil | Retention (%) after 4 weeks |
|---|---|---|---|
| 4-1 | — | — | 40 |
| 4-2 | 1% of phytic acid | 5% of soybean oil | 81 |

APPLICATION EXAMPLE 5

Testing of carotenoid-containing dry powders

Carotenoid-containing dry powders of working examples 5 and 6 were tested in respect of their stability in a premix of the following composition: 76% of wheat grits, 13.3% of choline chloride liquid (with 75% of choline chloride and 25% water) and 10% of the trace elements mix of application example 1. The premix was stored for 3 days, before 1% by weight of the carotenoid dry powder was mixed in. 1 g samples of the ready-prepared mixtures were tested in respect of their carotenoid content at the start and after 4 weeks storage in a conditioning cabinet at 40° C. and 70% relative humidity. The portion remaining after 4 weeks is reported as a percentage of the starting value of the storage in the following table:

| Working example No. | Active substance | Complexing agent | Oil | Retention (%) after 4 weeks |
|---|---|---|---|---|
| 5-1 | citranaxanthene | — | — | 22 |
| 5-2 | citranaxanthene | — | 5% soybean oil | 48 |
| 5-3 | citranaxanthene | 1% of sodium phytate | 5% soybean oil | 68 |
| 5-4 | canthaxanthene | 1% of EDTA sodium | 5% of soybean oil | 63 |
| 6-1 | canthaxanthene | — | — | 33 |
| 6-2 | canthaxanthene | 1% of phytic acid | 5% of soybean oil | 79 |

We claim:

1. A stable mixture containing an oxidation-sensitive compound selected from the group consisting of a fat-soluble vitamin and a carotenoid, a triglyceride, a complexing agent selected from the group consisting of phytic acid, phosphoric acid, meta-, pyro- or polyphosphoric acid and a salt thereof, and a coating substance.

2. A mixture as claimed in claim 1, which additionally contains an antioxidant.

3. A mixture as claimed in claim 1, wherein the triglyceride is a vegetable oil.

4. A mixture as claimed in claim 1, wherein the coating substance is a film former.

5. A mixture as claimed in claim 1, containing vitamin A or an ester thereof, phytic acid, a vegetable oil and gelatin.

6. A mixture as claimed in claim 1, in granular or pulverulent form having a particle size range of from 100 to 600 μm.

7. A process for preparing a mixture as claimed in claim 1, which comprises preparing a dispersion from an oxidation-sensitive compound, a triglyceride, a complexing agent and a coating substance and converting this dispersion by drying into a solid substance.

8. A process as claimed in claim 7, wherein an aqueous dispersion is prepared, dried and granulated or pulverized.

9. A mixture containing a triglyceride, a complexing agent selected from the group consisting of phytic acid, phosphoric acid, meta-, pyro- or polyphosphoric acid and a salt thereof, and a coating substance.

10. A mixture as claimed in claim 9, which additionally contain an antioxidant.

11. A mixture as claimed in claim 9, wherein the triglyceride is a vegetable oil.

12. A mixture as claimed in claim 9, wherein the coating substance is a film former.

13. A mixture as claimed in claim 9, containing phytic acid, a vegetable oil and gelatin.

14. A mixture as claimed in claim 9, in granular or pulverulent form having a particle size range of from 100 to 600 μm.

15. A process for preparing a mixture as claimed in claim 9, which comprises preparing a dispersion from a triglyceride, a complexing agent and a coating substance and converting this dispersion by drying into a solid substance.

16. A process as claimed in claim 15, wherein an aqueous dispersion is prepared, dried and granulated or pulverized.

* * * * *

UNITED STATES PATENT AND TRADEMARK OFFICE
CERTIFICATE OF CORRECTION

PATENT NO. : 4,929,774
DATED : May 29, 1990
INVENTOR(S) : Chiharu FUKAMACHI, et al It is certified that error appears in the above-identified patent and that said Letters Patent is hereby corrected as shown below:

On the title page, the date on the Priority Data is incorrect, it should read as follows:

--Japan    63-17232.........January 29, 1988--

Signed and Sealed this

Third Day of September, 1991

*Attest:*

HARRY F. MANBECK, JR.

*Attesting Officer*   Commissioner of Patents and Trademarks